(12) United States Patent
Smith

(10) Patent No.: US 6,537,823 B1
(45) Date of Patent: Mar. 25, 2003

(54) METHOD FOR DETECTION OF BROMINE IN URINE USING LIQUID CHEMISTRY DRY CHEMISTRY TEST PADS AND LATERAL FLOW

(75) Inventor: Jack V. Smith, Asheville, NC (US)

(73) Assignee: Sciteck Diagnostics, Inc., Arden, NC (US)

( * ) Notice: Subject to any disclaimer, the term of this patent is extended or adjusted under 35 U.S.C. 154(b) by 0 days.

(21) Appl. No.: 09/556,395

(22) Filed: Apr. 24, 2000

(51) Int. Cl.$^7$ .............................................. G01N 33/48
(52) U.S. Cl. ........................ 436/125; 422/56; 436/63; 436/166; 436/169
(58) Field of Search ...................... 422/56–61; 436/63, 436/124, 164, 166, 169, 816, 817, 901, 125

(56) References Cited

U.S. PATENT DOCUMENTS

| | | |
|---|---|---|
| 2,118,455 A | 5/1938 | Wallace |
| 3,530,957 A | 9/1970 | Shaw et al. |
| 3,603,957 A | 9/1971 | Merchant ................ 340/258 B |
| 4,234,316 A * | 11/1980 | Hevey ........................ 422/50 |
| 4,301,115 A | 11/1981 | Rapkin |
| 4,744,952 A * | 5/1988 | Ogita ......................... 422/56 |
| 5,447,837 A | 9/1995 | Urnovitz .................... 422/56 |
| 5,464,775 A | 11/1995 | Smith ......................... 436/63 |

OTHER PUBLICATIONS

Aldrich Chemical Company, inc,chemical catalog, p. 1398 in reference to the commercial availibility of 1,2,3, 4–tetrahydro–3–isoquinolinecarboxylic acid, no date supplied.*

* cited by examiner

*Primary Examiner*—Lyle A. Alexander

(57) ABSTRACT

This invention is in the field of toxicology and clinical diagnostics. More specifically, this invention provides a single dry chemistry, liquid chemistry, or lateral flow dry chemistry combination test device for use in the detection of adulteration by the addition of bromine(s) to a specimen submitted for Drugs of Abuse (DAU) testing and clinical diagnostic purposes in aqueous fluids, including urine, saliva, serum, blood, sweat extracts, and liquid homogenates of hair.

2 Claims, No Drawings

METHOD FOR DETECTION OF BROMINE IN URINE USING LIQUID CHEMISTRY DRY CHEMISTRY TEST PADS AND LATERAL FLOW

BACKGROUND OF THE INVENTION

1. Field of the Invention

As the use of illicit drugs in this country has increased, public concern over the problems associated with its effects has grown into a major concern. This concern has led to workplace drug testing in order to identify, treat, and remove active drug users from the workforce. This trend started in the military, and spread rapidly to law enforcement and any "safety-sensitive" private sector jobs such as airline pilots, truck drivers, and active crew members of public transportation. These initial strides into drug testing in the workplace revealed the obtrusive incursion of drug use and abuse in the daily lives of a significant portion of Americans. Further research indicated the staggering costs to public and private industry in terms of lost productivity, increased health care costs, and human suffering and death due to this scourge of drug abuse. As a result, drug testing has rapidly spread to all areas of the public and private sector. The vast majority of workplace drug testing has taken the form of urine testing, because of ease of collection, low cost, and effective indication of recent drug use. Other forms of testing include analysis of blood, saliva, sweat, and hair.

Because the effects of a positive test on the individual can be significant, and traumatic, the analysis procedures must guarantee accuracy with the emphasis on zero false positive results. On the other hand, all efforts must be made to detect all drug users in order to insure the success of this policy. These two requirements dictate a policy of close and vigorous scrutiny of the collection, testing, and reporting procedures. Juxtaposed to these closely monitored procedures is the deep and abiding desire of illicit drug users to avoid detection in order to keep their use secret, and to keep their jobs. Thus driven by these key desires, the ingenuity of a few in the drug abuse subculture has led to a plethora of ways to defeat the workplace drug testing procedures. These "adulteration" methods all conspire to produce the same desired effect: a false negative result which will protect the drug user's secret.

Adulteration techniques can be divided into two distinct types. The first utilizes an "in vivo" technique in which the user consumes the adulterant. The second technique utilizes an "in vitro" method in which the abuser adds the adulterant directly to the urine specimen submitted for testing.

The drug testing procedure involves two distinct parts. The initial segment is a panel of screening tests for the individual drugs. If a positive result is obtained in any of these initial tests, then a confirmation assay is performed for each drug that screened positive. Most adulteration techniques are aimed at the screening process, because of the inherent fragile nature of these inexpensive assays which adapt well to rapid, automated analysis techniques. All screening tests utilize antibody/antigen reactions quantified via an enzyme indicator. On the other hand, confirmation assays are labor and time intensive, highly accurate, expensive, and more difficult to adulterate. In addition, the positive screen has already raised a red flag, thereby drawing attention to the sample. The confirmation analysis utilizes GC-MS (gas chromatography mass spectrometry) testing which is considered the "gold standard" for drug assays scientifically and legally.

The "in vivo" methods function in one of three ways. These include dilution of the analyte of interest to a level below that required for a positive result, decreasing the time required to eliminate the consumed drug, or consuming a compound that will interfere with the screening method. Dilution is effected by consuming a large volume of liquid together with a diuretic to speed elimination of urine, and a B vitamin to add yellow color to the urine sample. Some commercial in vivo dilution products or "flushes" are sold under the following names: Carbo Clean, Test Pure, Kleen Test, Quick Flush, Naturally Klean, Test Free, UA Flush, Zydot's Special Blend, Daily Pure, Vale's Quick Clean, Test'n, and UR'n Kleen. Decreasing the elimination time will often enable the weekend drug user to avoid testing positive on a Monday morning drug test. This is accomplished by consuming acidic liquids (e.g. acidic fruit juices or ammonium chloride) to speed up elimination of basic drugs, or consuming basic liquids to speed up elimination of acidic drugs. Examples of an internally ingested substance which will disrupt the screening test procedure include aspirin and mefenamic acid, a prescription analgesic pain killer.

In vitro methods utilize literally hundreds of products and compounds that will adversely affect either the screening or confirmation process. Products affecting the screening process include many household products (i.e. all types of cleaners including hand, clothes and dishwashing detergents and soaps, table salt, hydrogen peroxide (oxidant), oxidants (such as sodium nitrite, sodium bromate, potassium bromate (Br), bleach (sodium hypochlorite (Cl), an oxidant), fingernail polish remover, vinegar, Drano, liquid plumber, sodium bicarbonate, Visine, fingernail polish, swimming pool cleaning chemicals and acid), or specialty products sold commercially as adulterants (i.e. Urine Luck (contains the oxidizer pyridinium chlorochromate), Purafyzit, Urine Sured, and THC Free are acid-based products with some including other ingredients such as chromates and nitrites (oxidants), UrinAid and Clear Choice are glutaraldehyde containing products, Amber-13 contains sulfides, Mary Jane Super Clean 13 is a soap, Stealth, and Toxiclean). Commercial products aimed at interfering with the confirmation process include nitrite (oxidant) containing products Klear and Whizzies and sodium bromate (oxidant) or potassium bromate (oxidant) containing product known as Stealth.

Substitution, or using a clean urine sample supplied by a third party, can be either in vivo or in vitro adulteration. In its simplest form, participants hide a clean urine in their clothing and put it into the specimen collection container (in vitro). Individuals requiring more stealth including those giving observed collections (military and corrections primarily) may substitute via the in vivo technique which requires putting the clean urine into the subject's bladder using a catheter.

Illicit drug users have learned to falsify urine screening tests by in vitro adulteration of urine samples by the addition of several readily available agents, including household products (soap, bleach, etc . . . ), hydrogen peroxide, and commercially available adulteration products, such as "UrinAid and Clear Choice" (glutaraldehyde containing adulterants) or "Urine Luck" (a chromate containing adulterant).

The vast majority of urine collections are not observed due to privacy issues. Collection facilities try to prevent in vitro adulteration or substitution by recording the temperature of the sample as soon as it is collected. It must fall inside the very narrow range of 90.5 to 99.8 degrees Fahrenheit. They also may require subjects to leave excessive clothing out of the collection room, and provide no hot water which prevents dilution of the sample with water. Obviously, however, it is very easy to secret small quantities of adulterating substances into the collection room. As little as a pinch of salt or a drop or two of glutaraldehyde, pyridinium chlorochromate or acid will affect most test screens. Because the effective amounts of most adulterants are very small, even observed collection as required by the military and criminal justice system can be defeated using the in vitro technique.

On the other hand, collection facilities currently have no weapons to detect in vivo adulterants, because they are consumed by the drug user several hours or days prior to collection of the sample. Currently only certain forms of adulteration as already mentioned can be detected in the laboratory.

All screening assays can be adulterated. These assays fall into three types of methods: florescent polarization immunoassay (FPIA), radioimmunoassay (RIA), and enzyme immunoassay (EIA, CEDIA, KIMS: Antibody/ agglutination). Toxicology and clinical chemistry literature includes numerous studies on the effects of adulterants on the screening technologies and the recommendation to test for their presence in urine samples. References include Mikkelsen and Ash, "Adulterants Causing False Negatives In Illicit Drug Testing", Clin. Chem. 34/11, 2333–2336 (1988); and Warner, "Interference of Common Household Chemicals In Immunoassay Methods For Drugs Of Abuse", Clin. Chem., 35/4, 648–651 (1989).

Accordingly, a need exists for providing an easy and convenient manner by which to make a determination of the presence of bromine containing (oxidative active) adulterants in urine samples which are being tested for drugs of abuse. Specifically an assay capable of detecting bromine. A further need exists for a convenient manner by which such determinations may be made by using rapid analysis manual techniques (such as a dipstick or lateral flow devices) and automated techniques that will advance the art significantly. And, the most important needs is for a device that would detect the adulterant bromine using just a single assay. This would be a marked advancement in the art and would result in the savings of millions of dollars to the drug testing laboratories required to perform adulteration testing and obviously this savings would be passed on to the end user (the businesses which initially request drug's of abuse assays on perspective and current employees). Other advancements that would be made with a device that is capable of the detection of different forms of bromine in urine in the form of sodium bromate, potassium bromate, or any compounds containing bromine that could be introduced into a urine in an effort to interfere with drugs-of-abuse testing. This is significant deterrent for a person trying to adulterate a urine sample with a bromine containing compound.

2. Description of the Related Art

This invention is in the field of toxicology. More specifically, this invention provides test strips (i.e. dry chemistry dipsticks, or on-site test modules utilizing thin layer chromatography in a lateral flow format, or other similar technology to the test strip) and liquid chemistry reagents for use in the detection of bromine with a single assay to include but not limited to sodium bromate, potassium bromate, analogs of these oxidants or other compounds containing bromine which are capable of producing an oxidative reaction in an aqueous solution which causes adulteration of immunoassays designed to detect Drugs of Abuse (DAU) in aqueous fluids to include but not limited to urine, saliva, serum, blood, sweat extracts, and liquid homogenates of hair.

Currently, all adulteration detection assays actually analyze the test sample itself for physical or chemical abnormalities. For instance, most of the adulteration products noted above can be identified by determining the pH, or specific gravity of the sample. These two assays will detect the presence of acids, bases, table salt, and high ionic strength soaps and detergents. It is important to note that there are no dry chemistry (dipstick or lateral flow technology) commercial tests available for oxidation-based adulterants (i.e. bromine, in the form of sodium bromate, potassium bromate, or other analog of bromine (which is contained in the commercially known product Stealth)). It is important to note that oxidative activity from an adulterant causes interference with the drugs-of-abuse immunoassays as known in the art as well as the extraction procedures used to extract drugs from urine. For example, lets say an employer suspects that an employee is under the influence of drugs while performing a sensitive job such as piloting a commercial jet, this individual (who has been smoking cannabinoids) is ordered to submit a urine for drug screening and adulterates his or her urine with nitrite. The urine which contains THC (cannabinoids) will be positive on the initial immunoassay screen. Because oxidants do not interfere with the initial screening process such as EIA (enzyme immunoassay) which is commonly used. The lab running the immunoassay drug screen will then forward the positive sample for confirmation by GC-MS (gas chromatography mass spectrometry). However, during the GC-MS extraction procedure the oxidant will interfere with the extraction process and prevent any THC from extraction from the urine for confirmation. The technician will run the sample on the GC-MS and the result will be negative for THC. The drug testing lab will have to report out a negative for the drug screen. This has obvious multiple negative effects on the industry. First, the drug abusers gets away with tampering with the sample, the lab runs the expensive procedure for confirmation by GC-MS and cannot report a positive and thus will get no revenue for running the confirmation procedure, and the employer who ordered the drug screen has an employee who is still under the influence and on the job, and lastly, the customers on the commercial jet are in for an interesting if not fatal ride. This is just one of many scenarios that could result from the use of oxidants for urine adulteration. It is also very important to note that there is no prior art that offers the capability of a single assay that detects bromine, more specifically in the form of bromine type oxidant.

The novel invention described herein describes a method to determine the presence or absence of bromine in urine or other fluids by liquid and dry chemistry test means which has not been taught prior to the present art. It should be noted that bromine is not normally found in urine.

The only published and patented chemical analysis methods for adulteration testing are liquid assays (aqueous not dry chemistry assays) for pH, specific gravity, glutaraldehyde and nitrite.

This new invention will clearly indicate if bromine is present in a sample of urine which will cause a false negative or false positive result depending upon the type of immunoassay used in the DAU screening process. Currently, the adulteration underground network produces two to five new methods to fool the drug tests each year. As a result drug testing facilities are forced to maintain a constant vigil for any unusual results. It is well known that adulteration of samples submitted for DAU testing cost the drug testing laboratories, employers, taxpayers and everyone involved in the drug screening process countless millions of dollars every year.

A thorough search of patents and research revealed no relative art (i.e., prior art) with any correlation to this technology. The art of testing for adulteration in urine as previously delineated in the literature describe various techniques including manual methods for measuring pH (meter or pH papers), specific gravity (via refractometer or dipstick), temperature, and liquid chemical analysis for specific adulterants such as glutaraldehyde (as described by U.S. Pat. No. 5,464,775). No reference, however, has described this new art as delineated here. The previous art will be enumerated here to further illustrate the unique advancement in the field of adulteration detection the present device yields. Other than U.S. Pat. No. 5,464,775 (which does not mention or teach any of the present art's indicators, or test means for the detection of adulterants containing bromine), none of the following patents teach the use of urine as the test subject of adulteration detection. It has been acknowledged in the art that random urinary sample matrices are very complex, and consist of many urinary constituents which create strong buffering and interference problems (e.g. cannibal like enzymes such as protease). In addition, disease states will significantly impact the nature of urinary contents. Urine is also the repository of all of the body's waste products including excess parent nutrients, vitamins, drugs, and their metabolites. These waste chemicals vary from person to person and significantly contribute to the individual uniqueness that makes assay design for urinary constituents more difficult than any other body fluid. All of these factors impact an assay's ability to obtain acceptable precision and accuracy. The ability of an assay to analyze a biological liquid such as saliva, therefore, rarely ever translates to an effective assay for urine. Therefore the present invention's ability to effectively cope with the random urine sample makes it unique.

Another patent, U.S. Pat. No. 3,603,957, discloses the use of assay test strips, but fails to teach a method for the determination of adulteration of a test sample submitted for drugs of abuse testing. It also doesn't teach a method to determine the presence or absence of any substance or adulterant which interferes with the drug's of abuse test assay such as oxidants. The patent doesn't teach the use of the present art's reaction formula to dry chemistry format called a dipstick or lateral flow technology that not only is completely novel, but prevents cross contamination between test pads typically found on a test strip (dipstick). In addition, this patent also failed to mention any methods for determination of adulteration of samples submitted for analysis of drugs of abuse by dipstick, lateral flow, colorimetric, liquid reagent (automated) or other suitable means.

Another patent, U.S. Pat. No. 4,301,115, discloses the use of assay test strips, and the ability of the assay strips to resist cross contamination between reactant areas (chemically impregnated test pads), but fails to teach a method for the determination of adulteration of a test sample submitted for drugs of abuse testing. The patent doesn't teach the use of the dry chemistry format utilizing either a dipstick or lateral flow device, liquid reagent (automated) method or mention any methods for determination of adulteration.

Another patent, U.S. Pat. No. 5,447,837, does mention the use of assay test strips but again fails to disclose a method for the determination of adulteration. This is a method for detection of an antigenic substance in human, biological samples. This patent also fails to mention the use of a reaction formula that is adaptable to the dry chemistry format utilizing either a dipstick or lateral flow device. It also doesn't teach a method to determine the presence or absence of any substance or adulterant which interferes with said reaction. In addition, this patent also failed to mention any methods for determination of adulteration of samples submitted for analysis of drugs of abuse by dry chemistry, liquid chemistry, calorimetric, or other suitable means.

Published literature and the prior art describes techniques such as ELISA that have been used to determine the presence of drugs of abuse, but these technologies have no relevant bearing on the present device. Previously taught technologies include measurement of pH (meter or pH papers), specific gravity (via refractometer or dipstick), temperature, and liquid chemical analysis for specific adulterants such as glutaraldehyde. Therefore, in a nutshell, the present device provides an absolute novel approach to adulteration testing and lateral flow testing using dry chemistry test pads and automated liquid reagent testing.

GC-MS, a confirmation, assay, is performed to verify the urines that screen positive for drugs of abuse. The GC-MS analysis costs 100 times as much as the initial screen ($100 vs $1). Every additional unnecessary GC-MS performed drives up the overall cost of drug testing. Eliminating these additional, unnecessary assays will save millions of dollars per year. False positive drug screens also strongly impact on-site testing. In most situations utilizing on-site tests (on site devices such as dipstick or lateral flow devices require no instrumentation, making these devices ideal for collection and on site facilities) the employee is screened upon arrival for work. If a positive is obtained using the on-site test, a second sample is forwarded to the lab for GC-MS confirmation and the employee is suspended from work or reassigned to other duties until the results of the test are known. Therefore, it is of vital importance that the employer and laboratory know if the sample has had an adulterant added, to save time, money, and possibly lives.

Not surprisingly, it is known and is illustrated here that a great need exists in the field of workplace drug testing for rapid, economical, and effective adulteration analysis of samples submitted for testing, whether liquid chemistry and/or dry chemistry methodology using dipsticks or lateral flow test devices (for single use and for on-site collections). The present invention does detect oxidants in the form of bromine effectively with a single assay and therefore and accordingly, the present device provides an easy and convenient manner by which to make a determination of the presence or absence of bromine oxidizing adulterants in samples submitted for drugs of abuse testing. The present art's use of lateral flow also enables the removal of any interference of any cross over of reagents or fluid from one test pad to another which is one of the exclusive problems with dipsticks.

It is clear that a need exists for a convenient manner by which a determination of intentional adulteration by the use of bromine (or analogs of bromine) oxidants can be made utilizing a rapid automated analysis utilizing a liquid reagent format of the present device or manual analysis in the form of dry chemistry (dipstick) or lateral flow test devices. These and other advances in the current state of the art will become evident in view of the present specification and claims.

SUMMARY OF THE INVENTION

Briefly stated, the present invention relates to the test devices for detecting the presence of an adulterant containing bromine or the presence of bromine for clinical purposes in a liquid test sample and the methods for making said devices. This invention is in the field of toxicology and clinical diagnostics. More specifically, this invention provides dry chemistry test strips (i.e. dipsticks, or dry chemistry and lateral flow [thin layer chromatography] test means) or automated or manual liquid reagent means for use in the detection of adulteration of human, biological samples (e.g. urine, blood, serum, saliva, sweat extracts, and hair homogenates) to be tested for DAU's via immunoassays. This invention achieves this goal by measuring the absence or presence of oxidants in the form of bromine (or analogs of bromine) in a test sample. And, this invention provides a unique method for preventing cross contamination between test pads (reactant areas) on dipsticks by the present inventions use of the dipstick test pad and lateral flow device technology. This invention provides a previously unavailable dry chemistry or liquid chemistry method for determining adulteration of a test sample by measuring the presence of bromine as required currently by the Department of Transportation, Nuclear Regulatory Commission, College of American Pathologist's Forensic Urine Drug Testing program, and the U.S. Department of Health and Human Service's SAMSHA program on all urines assayed for drugs of abuse under their protocols. And, this invention also provides a test means to detect bromine in a urine or other biological samples for clinical diagnostic purposes.

The present invention encompasses a method that can utilize several different techniques. The techniques would employ the manual method using dry chemistry dipsticks and the method of combining dry chemistry dipstick reactant areas (test pads) with lateral flow thin layer chromatography or the method of using a liquid reagent that is compatible with automated analyzers that provide high speed quantitative analysis which would be much less labor intensive than the manual methods providing a savings in time and money. For example, SAMSHA has made adulteration testing mandatory and the present art provides a novel method for performing adulteration testing for bromine containing oxidants (to include but not limited to sodium bromate, potassium bromate, bromate or bromine analogs, and Stealth) with or without the use of or need for instrumentation, thus allowing for the laboratory to suspend any further testing of a specimen failing an adulteration check. This course of action reduces technician time, and provides a significant economic savings. The widespread utility of the present art also provides the drug testing laboratory, collection site (where the urine is actually collected), or other users the choice of using the dry chemistry (manual) or automated liquid means which ever method best suits their situation or needs.

The present arts technique utilizes two dry chemistry techniques, one is dipsticks, which is a carrier dependent, rapid test that uses absorbent medium such as paper which have been impregnated with a chemical formulation to detect adulteration. After dipping one (dipstick) into a liquid test sample, a reaction takes place. Said resulting reaction will yield a color change indicating a positive or negative result (i.e. presence or absence of chromate, an adulterant). The other technique is the use of lateral flow in combination with a dry chemical test pad. The lateral flow device is a rapid test that uses absorbent medium such as paper which has been impregnated with the chemical formulation to detect adulteration. The paper, after impregnation, is then placed on a lateral flow medium, such as nitrocellulose paper, glass fiber paper, or other suitable wicking material that will deliver the test sample to the impregnated paper.

The lateral flow device works by dipping one end of the lateral flow device (LFD) into a sample (urine for example). The urine migrates up (along) the paper (or absorbent material) to the reactive sites (test paper) containing reagents (reactive ingredients). The urine constituents react with the assay reagents during the migration process and yield visible results. The urine can also be droppered onto the LFD and the sample will then migrate along the paper.

The ease of use and rapid results obtained by the present art's methodology illustrate the unique utility of this testing technique. In addition, very little technical expertise is required to perform this type of assay (no instrumentation required). Furthermore, the early detection of adulteration (prior to DAU screening) facilitates faster replacement with a fresh, untainted specimen from the participant, yielding more accurate information. This novel concept for adulteration monitoring provides an enormous savings of time and money. Adulteration testing utilizing these techniques are currently not available and have never been taught.

An important aspect of adulteration testing in urine is the sensitivity of the test method. Both techniques taught here have an effective sensitivity range comparable to the target immunoassay. The dipstick test and LFD dipstick hybrid (to be known as the LFD hybrid) have a quantitative to qualitative assay range. The results are evaluated via one of two categories: negative and positive.

The present arts technique also utilizes a liquid chemistry test means that allows for rapid analysis via an automated analyzer that can yield high speed quantitative results. This will result in rapid test results, improved accuracy, lowered labor cost, and better turn around on a high volume of test. This automated method is only limited by the speed of the automated analyzer. Some analyzers currently on the market are capable of over 10,000 test per a hour. The ability of the present art to perform a single assay on a high speed automated analyzer that is capable of detecting bromine or bromine containing adulterants has never been present or taught in the prior art.

It is currently known in the art that enzyme and antigen/antibody reaction kinetics are related to the rate of change in analytical, biological systems. The variables that affect this rate of change include concentration of reactants and product, temperature, pH, ionic strength, buffer strength, and other parameters. Many commercial and household adulterants dramatically affect the parameters noted above. The present art's innate and unique ability enables it to determine the presence of bromine (Stealth) in urine. As it is known in the art urine is a very complex matrix and the measurement of bromine in urine has to take into account many factors which will affect the assay.

The composition of the formulation to be applied to the dry chemistry dipstick, LFD hybrid and liquid chemistry method are composed of indicator(s) (visible colorimetric), and buffer(s).

Briefly stated, the present invention relates to test devices for measurement of bromine(s) in urine but could also work in other matrices such as blood, saliva, or other fluids that come from the human body and the procedures for making said test means. This invention is in the field of clinical diagnostics. More specifically, this invention provides dry chemistry dipsticks (DCD's or on-site test modules), thin layer lateral flow chromatographic dry chemistry technology (LFD's), and the combination of both in a unique hybrid that is not known prior to the present art and liquid chemistry reagents for automated and manual use. That is to say (in it's simplest terms) that this unique hybrid (LFD) will encompass the use of a dry chemistry test pad resting on the surface of a wicking material (such as nitrocellulose) acting as a fluid delivery device. This new art can utilize aqueous, biological specimens including urine, saliva, sweat extracts, blood, and serum. Thus, this invention provides a unique method for bromine (oxidant) measurement utilizing rapid test devices including the automated method as well as the DCD, and LFD methodology thereby enabling in-home testing through over-the-counter (OTC) sales. This is an enormous advancement in the art. These advances and improvements of the present device over the prior art provides the health care and drug testing industry with powerful new clinical and diagnostic tools.

A thorough search of the literature reveals no relative art resembling this technology; therefore, this invention is clearly a novel creation, and is not obvious to anyone skilled in the art of toxicology and clinical chemistry.

DETAILED DESCRIPTION OF THE INVENTION

This instant invention is a single assay in the form of a liquid chemistry reagent, dry chemistry dipstick or lateral flow device in conjunction with using a dry chemistry test pad for the detection of oxidants in the form of bromine or analogs of bromine (or other states of bromine such as sodium bromate, potassium bromate, etc.) in sample matrices consisting of urine or other biological specimens (e.g. saliva, serum, blood, sweat extracts, and hair homogenates). The bromine adulteration detection assay that makes up the instant invention may take the form of dry chemistry dipsticks or dry chemistry test pad lateral flow hybrid, both of which are composed of some or all of the following compounds: buffer(s) and color indicator(s), hereinafter referred to as the adulteration reagent or the liquid automated reagent designed for high speed automated analyzers also composed of some or all of the following compounds: buffer(s) and color indicator(s). It can be noted that the liquid reagent method could also be used manually employing spectrophotometers or other types of visual detection technology. Buffering of the reactants is critical to the adulteration reagent, because pH plays a vital role in the reaction kinetics. In the case of the dipstick and the dipstick/lateral flow hybrid (which can be known as the "DLFH" device), bromine adulteration reagent components are impregnated on the test strip pad composed of solid, absorbent carrier(s), usually known as test pads. In the case of dipsticks, these test pads are typically affixed to a solid support (usually plastic). This device is then submerged in the liquid test sample, removed, and a measurable (i.e. visible) response is observed. Or in the case of the DLFH, the dry chemistry test pad is chemically impregnated identically to the dipstick. The test pad is then placed in fluid (direct) contact with lateral flow paper (such as nitrocellulose). This device is then exposed to a fluid (urine for example). The urine then migrates to the location of the test pad, saturates the test pad, and the reaction takes place.

The adulteration reagents of the device constitute the heart of the analytical response provided by it, and is comprised of one or more reagent compositions responsive to any number of chemical components capable of adulterating a test sample. The reagents, in the broadest sense produces a detectable manifestation of the presence of said chemical component(s); said chemical components being capable of adulterating a test sample thereby yielding an incorrect result (interfering with) for the target DAU immunoassay. The response can be in the form of the appearance or disappearance of a color, or the changing of one color to another. Said measurable response may also be evidenced by a change in the amount of light reflected or absorbed during the reaction of interest. The analytical arts are replete with examples of these types of detectable responses.

In the present invention, there is provided a dry chemistry test strip in the form of a dipstick or DLFH for the detection of adulteration in urine (or other biological fluids including saliva, sweat extracts, serum, blood, and hair homogenates) comprising a solid, carrier matrix in the form of a dry chemistry dipstick containing an indicator compound and buffer.

The present technology does not predict or forecast the obvious advancement in the art to encompass the present invention, nor does it hint at the extraordinary improvement the present invention provides in the field of adulteration detection. While urine is the sample matrix of choice for this instant invention (and for the immunoassays currently in general use) it is well within the scope of this novel invention to utilize it in the analysis of other sample matrices including saliva, sweat extracts, serum, hair homogenates, gastric contents, cerebral spinal fluid, and blood. While the assay is designed for adulteration detection, the assay could be used in other fields for other uses such as clinical diagnostics, manufacturing, or research.

The remarkable discovery of the new art formula will require the presence of an indicator(s) for bromine in urine (as well as the other matrices mentioned) that was unknown prior to this art. The newly discovered and suitable indicators for the present art formula are; 1,2,3,4-tetrahydrobenzo(h)quinolin-3-ol, 1,2,3,4-tetrahydrobenzo(h)quinolone, 1,2,3,4-tetrahydrobenzo(h)quinaldine, 3-hydroxy-1,2,3,4-tetrahydrobenzo(h)quinolone, 3-hydroxy-N-methyl-1,2,3,4-tetrahydrobenzo(h)quinolone, 3-acetoxy-N-methyl-1,2,3,4-tetrahydrobenzo(h)quinolone, N-methyl-1,2,3,4-tetrahydrobenzo(h)quinolone, 1,3-phenylenediamine, 1,2,3,4-tetrahydroquinoline, 1,2,3,4-tetrahydroisoquinoline hydrochloride, 7,8-benzoquinoline, 1,2,3,4-tetrahydro-3-isoquinolinecarboxylicacid hydrochloride, 1,2,3,4-tetrahydro-1-napthylamine hydrochloride, napthylamine, N,N-dialkyl-alpha-napthylamine, phenolphthalin, 2,2'-Azino-di-(3-ethylbenzthiazolinesulfonic acid), 2,2'-Azino-di-(3-ethylbenzthiazolinesulfonic acid) diarmronium salt, cyanoditoly tetrazolium chloride, 3,3'-diaminobenzidine, o-dianisidine, dimethoxybenzidine, 0-phenylenediamine, 3-amino-9-ethylcarbazole, 3,3'-5,5'-tetramethylbenzidine, dimethoxybenzidine, 8-hydroxyquinoline, m-phenylenediamine, 3-dimethylaminobenzoic acid, 5-aminosalicylic acid, and 4-chloro-1-napthol, and another indicator that is suitable for the present device is 4-aminoantipyrine in combination with one of the following compounds; p-hydroxybenzene sulfonate, p-hydroxybenzoic acid, n-ethyl-n-(2-hydroxy-3-sulfopropyl)-m-toluidine, n-ethyl-n-sulfopropyl-m-toluidine, 2-hydroxy-3,5-dichlorobenzenesulfonic acid, 3-hydroxy-2,4,6-triiodobenzoic acid, and 3-hydroxy-2,4,6-tribromobenzoic acid. In addition, some of the above indicators require a diazotizable amine in the form of sulfanilic acid, arsanilic acid, sulfanilamide, aminobenzoic acid, or other suitable amine. It is understood that the present arts discovery of the use of indicators such as the ones mentioned above or others that have not been mentioned that are sensitive to bromine oxidation-reduction reactions in biological matrices such as urine and are capable of producing a detectable response in the presence of a bromine oxidation-reduction reaction are within the present art. Therefore the use of a bromine oxidation-reduction indicator that is not mentioned here would fall within the spirit and scope of the present invention.

This new art formula will require appropriate buffering. Suitable buffers may include any of the following (referred to here by their commonly used acronyms): citrate, borate, borax, sodium tetraborate decahydrate, sodium perchlorate, sodium chlorate, sodium carbonate, (Tris[hydroxymethyl] aminomethane), MES (2-[N-Morpholino]ethanesulfonic acid), BIS-TRIS (bis[2-Hydroxyethyl]iminotris [hydroxymethyl]methane;2-bis[2-Hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylarmino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hydroxy-1,1-bis (hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris (Hydroxyetbyl)methylamino]-2-hydroxypropanesulfonic acid), HEPPSO (N-[2-Hydroxythyl]piperazine-N'-[2Hydroxypropanesulfonic acid]), POPSO (Piperazine-N, N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hydroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylarnino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, succinic acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, citric acid, oxalic acid, tartaric acid, oxalate or succinate. Other buffers with an effective pK and pH range, and capacity suitable for maintaining the sample-reagent mixture within the required parameters of the assay's reaction mechanism may be added to the above group, however acidic buffers are preferred.

Manufacture of the dry chemistry dipsticks may require the addition of thickeners as taught in the art. Some compounds commonly used for this purpose include: polyvinylpyrrolidone, algin, carragenin, casein, albumin, methyl cellulose, and gelatin. The typical range of concentration for these thickeners is about 0.5 to 5.0 g. per 100 ml. Wetting agents or surfactants are also typically used in dry chemistry. For dry chemistry applications, wetting agents aid in even distribution of the chemicals and promote even color development. Acceptable wetting agents can be hydrophilic polymers, or cationic, anionic, amphoteric, or non-ionic species. Some commonly used wetting agents include sodium dodecyl-benzene sulphonate, sodium lauryl sulphate, benzalkonium chloride, N-lauroylsarcosine sodium salt, Brij-35, Tween 20, Triton X-100, dioctyl sodium sulphosuccinate, and polyethylene glycol 6000. Wetting agents can be added to dipstick impregnation solutions in amounts of 0.5% to 5.0%, and 0.1% to 1.0% in liquid reagents.

Color enhancers may be used such as sucrose, lactose, glucose or other compounds. Color enhancement can be defined as intensification and/or alteration in some manner the color that is produced by the reaction to improve the measurement of the detectable response.

The production of dry chemistry test strips for the present invention can utilize any form of absorbent, solid phase carrier including filter paper, cellulose or synthetic resin fleeces in conjunction with liquid solutions of reagent compositions in volatile solvents. This can be carried out in one or more impregnation steps. Each impregnation may contain one or more of the chemical compounds making up the assay reagent composition; the exact procedure is dictated by the inter-reactivity of the assay constituents and the order in which they may have to react with the analyte of interest.

In the case of the DLFH, the lateral flow invention it can utilize any form of absorbent, solid phase carrier that is capable of transporting a fluid. These can include filter paper, cellulose or synthetic resins. More specifically, the lateral flow material can include cellulose, cellulose acetate, nitrocellulose, mixed ester, teflon, polyvinylidene difluoride (PVDF), polytetrafluoroethylene (PTFE), polysulfone, cotton linter, non-woven rayon, glass fiber, nylon, ion exchange or other suitable membranes or solid support.

After impregnation, the dipsticks are dried, cut into strips, glued to a support structure (usually a flexible, flat, plastic stick) as part of a "sandwich" composed of the handle, test pad, and a synthetic resin film and/or a fine-mesh material in the manner described in German Pat. No, 2,118,455. In addition, the instant invention may be combined with the water-stable film as taught in U.S. Pat. No. 3,530,957 to produce a dipstick in which the excess sample fluid can be wiped off in order to improve the accuracy and precision of the results.

The following examples are provided to further illustrate the inventive aspects of the present discovery, and to further exemplify preferred embodiments. As such, they are intended as merely illustrative, and are not to be construed as limiting the scope of the claims appended hereto.

EXAMPLE 1

This is a method for manufacturing a dry chemistry dipstick (test strip) with a solid carrier for the detection of bromine in urine samples. Filter paper is successively impregnated with the following solutions and dried at 25 degree C.:

Solution I citric acid 21.0 g p-arsanilic acid 3.0 g 1,2,3,4-tetrahydrobenzo(h)quinolin-3-ol 7.0 g add propanol to make 1000 mL total volume of solution In this example a dipstick was prepared in accordance with the instant invention. The device comprised a paper carrier or solid matrix incorporated with the composition of solution 1 above. Note that the concentrations of any of the following examples can be varied to suit the dipstick device format (dependent upon paper type, or use of semi-permeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. The dried paper is then laminated to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine submitted for drugs of abuse testing, and no uniform blue to purple color develops then no bromine is present. Conversely, if any concentration of bromine are present in the urine at a 0.01% concentration or greater a blue to purple color will develop thus confirming the presence of bromine. The color can vary dependent upon a variety of factors such as color of urine, concentration of urine, indicator used, etc.

In summary, Example 1 is as follows: the foregoing dry chemistry test strip (dipstick) method for the detection of bromine in a sample of urine comprises the steps of preparing a test means by successively impregnating a solid, carrier matrix with reagent solutions, drying the impregnated, solid test means, then dipping said dried test means into urine, and finally observing any color change in the presence or absence of bromine.

The following changes to the above reagent solution will remain within the scope and function of this invention and will have similar results to the example above. The indicator pair in solution 1, p-arsanilic acid and 1,2,3,4-tetrahydrobenzo(h)quinolin-3-ol, could be substituted with one or more of the following compounds including 1,2,3,4-tetrahydrobenzo(h)quinolone, 1,2,3,4-tetrahydrobenzo(h)quinaldine, 3-hydroxy-1,2,3,4-tetrahydrobenzo(h)quinolone, 3-hydroxy-N-methyl-1,2,3,4-tetrahydrobenzo(h)quinolone, 3-acetoxy-N-methyl-1,2,3,4-tetrahydrobenzo(h)quinolone, N-methyl-1,2,3,4-tetrahydrobenzo(h)quinolone, 1,3-phenylenediamine, 1,2,3,4-tetrahydroquinoline, 1,2,3,4-tetrahydroisoquinoline hydrochloride, 7,8-benzoquinoline, 1,2,3,4-tetrahydro-3-isoquinolinecarboxylic acid hydrochloride, 1,2,3,4-tetrahydro-1-napthylamine hydrochloride, napthylamine, N,N-dialkyl-alpha-napthylamine, phenolphthalin, 2,2'-Azino-di-(3-ethylbenzthiazolinesulfonic acid), 2,2'-Azino-di-(3-ethylbenzthiazolinesulfonic acid), 2'-Azino-di-(3-ethylbenzthiazolinesulfonic acid) diammonium salt, cyanoditoly tetrazolium chloride, 3,3'-diaminobenzidine, o-dianisidine, dimethoxybenzidine, m-phenylenediarnine, 3-amino-9-ethylcarbazole, 3,3'-5,5'-tetramethylbenzidine, dimethoxybenzidine, 8-hydroxyquinoline, o-phenylenediamine, 3-dimethylaminobenzoic acid, 5-aminosalicylic acid, and 4-chloro-1-napthol, and another indicator that is suitable for the present device is 4-aminoantipyrine in combination with one of the following compounds; p-hydroxybenzene sulfonate, p-hydroxybenzoic acid, n-ethyl-n-(2-hydroxy-3-sulfopropyl)-m-toluidine, n-ethyl-n-sulfopropyl-m-toluidine, 2-hydroxy-3,5-dichlorobenzenesulfonic acid, 3-hydroxy-2,4,6-triiodobenzoic acid, and 3-hydroxy-2,4,6-tribromobenzoic acid. In addition, some of the above indicators require a diazotizable amine in the form of sulfanilic acid, arsanilic acid, sulfanilamide, aminobenzoic acid, or other suitable amine.

The citric acid buffer in solution 1, may be substituted with one or more of the following buffers: borate, borax, sodium tetraborate decahydrate, sodium perchlorate, sodium chlorate, sodium carbonate, MES (2-[N-Morpholino]ethanesulfonic acid), BIS-TRIS (bis[2-Hydroxyethyl]iminotris[hydroxymethyl]methane;2-bis[2-Hydroxyethyl]amino-2-[hydroxymethyl-1,3-propanediol), ADA (N-[2-Acetamidol]-2-iminodiacetic acid; N-[Carbaoylmethyl]iminodiacetc acid), ACES (2-[(2-Amino-2-oxoethyl)amino]ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl)methylamino]propane), BES (N,N-bis[2-Hydroxyethyl]-2-aminoethaesulfonic acid; 2-bis(2-Hydroxyethyl)amino]ethanesulfonic acid), MOPS (3-[N-Morpholino]propanesulfonic acid), TES (N-tris[Hydroxymethyl]methyl-2-aminomethanesulfonic acid; 2[2-Hysroxy-1,1-bis(hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris(Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl]methyllycine; N-[2-Hydroxy-1-1-bis(hydroxymethyl)etyyl]glycine), BICINE (N,N-bis[2-Hydroxyethyl]glycine), TAPS (N-tris[Hydroxymethyl]methyl-3-aminopropanesulfonic acid; ([2-Hydroxy-1,1-bis(hydroxymethyl)ethyl]amino)-1-propanesulfonic acid), AMPSO (3-[(1,1-Dimethyl-2-hydroxyethyl)amino]-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate, tartaric, or succinate. Or other buffers with an effective pK and pH range, and capacity suitable for maintaining the sample-reagent mixture within the required parameters of the assay's reaction mechanism may be added to the above group, however acidic buffers are preferred.

EXAMPLE 2

This is a method for manufacturing a liquid, carrier-free reagent for the adulteration detection of bromine in urine.
Prepare a solution containing:
Bromine Solution I (R1)
  HCl (hydrochloric acid concentrate) 21.0 mL
  1,3-benzenediamine 2.1 g
  distilled water added to 1000 mL total volume of solution
  pH the solution to a value of approximately 2.0
  lab notes: a) Buffer strength is preferably 0.001 Molar or greater
Bromate Calibrator Formulations
  Zero (0) calibrator:
    1 liter of 0.2 micron filtered normal human urine with no adulterants or drugs present, and 0.01% sodium azide.*
  5.0% calibrator:
    1.0 mg/dl potassium bromate**
    1.5 g monosodium phosphate*** page 26
100 mL of 0.2 micron filtered normal human urine with no adulterants or drugs present*
pH the solution to a value between 3.0 and 11.0
lab notes:* Human urine can be substituted with distilled water, synthetic urine or other suitable solvent. The bacterial inhibitor sodium azide could be replaced with chloroamphenicol or other suitable bacterial inhibitors that would inhibit the growth of bacteria.
** Potassium chromate could be substituted with any suitable concentration of oxidant as a calibrator such as bleach, nitrite, hydrogen peroxide (stabilized preferably) or other oxidants
*** The monosodium phosphate buffer could be substituted with any suitable buffer such as the ones mentioned above that would place the liquid solution at an appropriate pH that is suitable with the calibrator being used (note that these different bromates would required different pH ranges for stability) and would in addition aid in stabilizing the calibrator in solution.

The reagent system of the instant invention (liquid reagent) is intended for use on any automatic chemistry analyzers with open channel capability including Olympus AU 5000 series, Hitachi 700 series, and many others. The reagent as outlined in Example 2 is used in the following manner: the one component of the reagent composition (R-1) is placed in the reagent compartment of the analyzer; samples, calibrators, and controls are aliquoted into sample cups which are then placed on the analyzer. An aliquot of 10 uL of each specimen is then pipetted into a single, discrete cuvette followed by the addition of 125 uL of the first reagent, R-1, and mixed; A first spectrophotometer reading is then taken followed by a second after a specified incubation period (i.e. one minute for this example) at the specified wavelength (between 340 and 800 nm). The spectrophotometer readings are then recorded. In this instance the assay is read at 415 nm, 540 nm or 660nm. The absorbance can vary from spectrophotometer based on differences in the width of cuvette, bulb strength, filter used, and detectors used to name a few. The absorbance of samples, and controls are printed and then compared to the calibrator's absorbance. The quantitative value for bromine concentration is then calculated. Any concentration of bromine greater than 1.0 mg/dL is considered adulterated.

Please note that in some cases an adulterant or abnormal constituent in a sample may cause a false positive. This scenario will yield a very significant increase in the cost of analysis, because a GC-MS assay must then be performed to verify the screening positive. The GC-MS analysis costs 100 times as much as the screen ($100 vs $1). Every additional unnecessary GC-MS performed drives up the overall cost of drug testing. Eliminating these additional, unnecessary assays will save millions of dollars per year. False positive drug screens also strongly impact on-site testing. In most situations utilizing on-site tests, the employee is screened on arrival for work. If a positive is obtained using the on-site test, a second sample is forwarded to the lab for GC-MS confirmation and the employee is suspended from work or reassigned to other duties until the GC-MS results are known. If the positive is a false one due to interference with the screen, the emotional and financial losses sustained by the worker can be extremely detrimental. The company's morale and financial well-being are also harmed. It is, therefore, very important to be able to identify a sample that will produce a false positive.

Specifications for running urine samples vary from instrument to instrument. Listed below is an example of parameters for the Hitachi 700 series analyzer. The settings are intended as guidelines, and are set forth with the understanding that all those skilled in the art would recognize that such parameters will vary from instrument to instrument. The suggested specifications for the Hitachi 700 series are as follows:

| Parameter settings for the Hitachi 700 series | |
|---|---|
| Test: | [BR] |
| Assay code: | [1 POINT] [50] - [0] |
| Sample volume: | [7] [5] |
| R1 volume | [210] [100] [NO] |
| R2 volume | [0] [100] [NO] |
| Wavelength | [0] [660] |
| Calib. Method: | [Linear] [0] [0] |
| Std. (1) Conc.-POS: | [0.0] *- [1] * assigned calibrator value |
| Std. (2) Conc.-POS: | [1.0] - [2] assigned calibrator value |
| | page 28 |
| Std. (3) Conc.-POS: | [ ] - [ ] |
| Std. (4) Conc.-POS: | [ ] - [ ] |
| Std. (5) Conc.-POS: | [ ] - [ ] |
| Std. (6) Conc.-POS: | [ ] - [ ] |
| SD Limit: | [999] |
| Duplicate Limit: | [32000] |
| Sensitivity Limit: | [0] |
| ABS. Limit (INC/DEC): | [32000] [INCREASE] |
| Prozone Limit: | [0] [lower] |
| Expected Value: | [0.0] - [1.0] |
| Tech. Limit: | [0] - [1000] |
| Instrument Factor | [1.0] |

Note: this assay is to be performed at the same temperature used for the DAU testing, usually 37 degrees Centigrade. However, this can vary without affecting the assay. The temperature could be between refrigerated to 45 degrees Centigrade.

Thus as described above, an unknown urine submitted for drugs of abuse testing with no bromine present, will produce a value of less than the 1.0% Bromine calibrator. Conversely, if the sample has a concentration of greater than 1.0% Bromine then it is an unacceptable sample and will result in false negative drug test results. Further testing can determine which of the above causes have produced the unacceptable specimen, however, it is irrelevant to the overall task at hand, which is to determine the suitability of a specimen for drugs of abuse testing.

To summarize more specifically Example 2, the automated method for the detection of adulteration of an unknown sample of urine submitted for drugs of abuse immunoassay testing comprising the steps of placing aliquots of an unknown urine (or other biological sample i.e. serum, whole blood, cerebral spinal fluid, gastric fluid, hair homogenates, sweat extracts, saliva or other biological fluid) and calibrator to be tested in automated analyzer sampling cups, placing the cups in a sampling tray within an automated analyzer, transferring the aliquots of sample and calibrator to cuvettes mounted within the automated analyzer, injecting a first reagent composition (R-1) comprising an indicator and buffer in an aqueous medium into the cuvettes, mixing sample and reagent, and mixing sample and reagents, and reading absorbance values of reaction mixture composed of reagents and test samples (said test samples include urine specimens, controls, and calibrator) at specified intervals, in accordance with a preprogrammed code introduced into the automated analyzer, at a preprogrammed monochromatically specified wavelength, and comparing absorbance of the first reagent composition plus the unknown samples with that of the first reagent composition plus the calibrator containing a zero reference point (normal urinary matrix), and thereby determining the presence or absence of oxidants which adversely affects the reaction kinetics of the DAU assay being used by the drug testing laboratory.

The following changes to the above reagent solutions will remain within the scope and function of this invention and will have similar results to the example above. The indicator in the solution 1,1,3-benzenediamine, could be substituted with one or more of the following compounds including could be substituted with one or more of the following compounds including 1,2,3,4-tetrahydrobenzo(h)quinolone, 1,2,3,4-tetrahydrobenzo(h)quinaldine, 3-hydroxy-1,2,3,4-tetrahydrobenzo(h)quinolone, 3-hydroxy-N-methyl-1,2,3,4-tetrahydrobenzo(h)quinolone, 3-acetoxy-N-methyl-1,2,3,4-tetrahydrobenzo(h)quinolone, N-methyl-1,2,3,4-tetrahydrobenzo(h)quinolone, 1,2,3,4-tetrahydroquinoline, 1,2,3,4-tetrahydroisoquinoline hydrochloride, 7,8-benzoquinoline, 1,2,3,4-tetrahydro-3-isoquinolinecarboxylicacid hydrochloride, 1,2,3,4-tetrahydro-1-napthylamine hydrochloride, napthylamine, N,N-dialkyl-alpha-napthylamine, phenolphthalin, 2,2'-Azino-di-(3-ethylbenzthiazolinesulfonic acid), 2,2'-Azino-di-(3-ethylbenzthiazolinesulfonic acid), 2'-Azino-di-(3-ethylbenzthiazolinesulfonic acid) diammonium salt, cyanoditoly tetrazolium chloride, 3,3'-diaminobenzidine, o-dianisidine, dimethoxybenzidine, m-phenylenediamine, 3-amino-9-ethylcarbazole, 3,3'-5,5'-tetramethylbenzidine, dimethoxybenzidine, 8-hydroxyquinoline, o-phenylenediamine, 3-dimethylaminobenzoic acid, 5-aminosalicylic acid, and 4-chloro-1-napthol, and another indicator that is suitable for the present device is 4-aminoantipyrine in combination with one of the following compounds; p-hydroxybenzene sulfonate, p-hydroxybenzoic acid, n-ethyl-n-(2-hydroxy-3-sulfopropyl)-m-toluidine, n-ethyl-n-sulfopropyl-m-toluidine, 2-hydroxy-3,5-dichlorobenzenesulfonic acid, 3-hydroxy-2,4,6-triiodobenzoic acid, and 3-hydroxy-2,4,6-tribromobenzoic acid. In addition, some of the above indicators require a diazotizable amine in the form of sulfanilic acid, arsanilic acid, sulfanilamide, aminobenzoic acid, or other suitable amine.

The hydrochloric acid buffer in solution 1, may be substituted with one or more of the following buffers: citrate, borate, borax, sodium tetraborate decahydrate, sodium perchlorate, sodium chlorate, sodium carbonate, MES (2-[N-Morpholino]ethanesulfonic acid), (Tris[hydroxymethyl] aminomethane), .BIS-TRIS (bis[2-Hydroxyethyl]iminotris [hydroxymethyl]methane; 2-bis[2-Hydroxyethyl]amino-2-[hydroxymethyl-1,3-propanediol), ADA (N-[2-Acetamidol]-2-iminodiacetic acid; N-[Carbaoylmethyl] iminodiacetc acid), ACES (2-[(2-Amino-2-oxoethyl)amino] ethanesulfonic acid; N-[2-Acetamido]-2-aminoethanesulfonic acid), PIPES (PiperazineN-N'-bis[2-ethanesulfonic acid)]; 1,4-Piperzinedethanesulfoic acid), MOPSO (3-[N-Morpholinol]-2-hydroxypropanesulfonic acid), BIS-TRIS PROPANE (1,3-bis[tris(Hydroxymethyl) methylamino]propane), BES (N,N-bis[2-Hydroxyethyl]-2-aminoethaesulfonic acid; 2-bis(2-Hydroxyethyl)amino] ethanesulfonic acid), MOPS (3-[N-Morpholino] propanesulfonic acid), TES (N-tris[Hydroxymethyl]methyl-2-aminomethanesulfonic acid; 2[2-Hysroxy-1,1-bis (hydroxymethyl)-ethyl]amino)ethanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris (Hydroxyethyl)methylamino]-2-hydroxypropanesulfonic acid), HEPPSO (N-[2-Hydroxythyl]piperazine-N'-[2Hydroxypropanesulfonic acid]), POPSO (Piperazine-N,N'-bis[2-hydroxypropanesulfonic acid]), EPPS (N-[2-Hydroxyethyl]piperazine-N'-[3-propanesulfonic acid), TEA (triethanolamine), TRICINE (N-tris[Hydroxymethyl] methyllycine; N-[2-Hydroxy-1-1-bis(hydroxymethyl)etyyl] glycine), BICINE (N,N-bis[2-Hydroxyethyl]glycine), TAPS (N-tris[Hydroxymethyl]methyl-3-aminopropanesulfonic acid; ([2-Hydroxy-1,1-bis(hydroxymethyl)ethyl]amino)-1-propanesulfonic acid), AMPSO (3-[(1,1-Dimethyl-2-hydroxyethyl)amino-2-hydroxypropanesulfonic acid), CHES (2-[N-Cyclohexylamino]ethanesulfonic acid), CAPSO (3-[Cyclohexylamino]-2-hydroxy-1-propanesulfonic acid), AMP 2-Amino-2-ethyl-1-propanol, CAPS (3-[cyclohexylamino]-1-propanesulfonic acid), hydrochloric acid, phosphoric acid, lactic acid, sulfuric acid, nitric acid, chromic acid, boric acid, perchloric acid, potassium hydrogen tartrate, potassium hydrogen phthalate, calcium hydroxide, phosphate, bicarbonate, sodium hydroxide, potassium hydroxide, oxalate or succinate. Other buffers with an effective pK and pH range, and capacity suitable for maintaining the sample-reagent mixture within the required parameters of the assay's reaction mechanism may be added to the above group, however acidic buffers are preferred.

EXAMPLE 3

This example will illustrate in detail the exact method for manufacturing the lateral flow bromine method. Keep in mind this method could be utilized for any general chemistry "test pad" or pads that are currently used or will be used in the art. In the case of DLFH technology, the manufacturing process includes impregnating onto an absorbent, solid carrier (e.g. paper) called in this example, the "test pad", in exactly the same manner as Example 1 with similar constituents. The test pad, once impregnated, is dried, then mounted onto a solid support (nitrocellulose membrane) that is capable of transporting (through lateral flow) liquid to the test pad from the point of application of a test sample. In simpler terms, the device is dipped into a liquid or the liquid sample is placed on the device at the bottom or starting point for the assay. The liquid migrates from the starting application point to the opposite end of the nitrocellulose lateral flow paper, during which the test pad becomes saturated with the sample. The reaction takes place on the test pad and color develops. The developed color is then compared to a color chart with known concentrations of bromine that has the appropriate colors relative to each specific concentration of bromine(s). The results are then recorded. Note, the test pad must be an absorbent (wicking) material that permits migration of sample up the solid absorbent test pad and allows analytes and reactants to interact.

Absorbent material is successively impregnated with the following solutions and dried at 25 degree C.:
Solution 1
  napthylamine 2.0 g
  aminobenzoic acid 6.0 g
  oxalic acid 12.6 g
  pH solution to a pH of 2.0
  lab notes: the pH of the 1 liter solution should be acidic In this example, the lateral flow device is prepared in accordance with the instant invention. The lateral flow device is comprised of a paper carrier matrix (S&S, 593 grade filter paper) impregnated with the compositions of solution 1. The paper is then cut into test pads 5 mm by 5 mm. Note that said concentrations of any of the above constituents can be varied to suit the DLFH lateral flow/dipstick device format (e.g. dependent upon paper type, and inclusion of semi-permeable membranes or other innovations utilized in dry chemistry technology). The paper is then dried using forced air. The dried impregnated test pad is then placed at approximately 35 mm (in the middle) of a 5 mm wide by 70 mm long nitrocellulose membrane (S&S Fast-Track™ NC) and makes fluid contact with nitrocellulose lateral flow paper. The nitrocellulose membrane is capable of transporting a liquid by capillary action or wicking from one end of the lateral flow device to the other in approximately 60 seconds. In this example, the DLFH has the dimensions of 5 mm wide by 70 mm long and can be backed by or in contact with strips of glass fiber filter material (e.g. S&S 30 grade) to aid in controlling the wicking action, or other solid support material can be used.

Again, to completely illustrate the present device the starting point or origin at which the sample is placed on the test device is 5 mm from one end of the strip, and 35 mm from the site of where the test pad is placed in fluid contact with the strip. For simplicity, this example will have the 5 mm by 5 mm impregnated test pad placed on top of the lateral flow paper and thus be in fluid contact with the said paper.

The mechanics of how the present art's LFD and dipstick test pad hybrid may be explained is as follows. The starting point or origin at which the sample is placed on the test device is 5 mm from one end of the strip, and 35 mm from site where the chemically impregnated test pad is in fluid contact with the lateral flow paper. The test pad can be placed on top of the lateral flow paper making fluid contact with the lateral flow paper from the bottom side of the test pad, or the lateral flow paper can touch the paper from the side of the test pad and remain in fluid contact with the test pad. Or the lateral flow paper can rest on top of the edge of test pad or be attached and in fluid contact with the test pad in some other manner. One of the novel advantages in using a hybrid device made of lateral flow material and a dry chemistry test pad is the lack of cross contamination from one pad to the next from excessive fluid, as is inherent in the prior art. For illustration, currently there are available many different types of dry chemistry test strips available, such as the Miles Laboratories, Inc. MULTISTIX®. This device and many other like it has multiple reagents test pads with different chemistries impregnated onto each pad on a single support membrane backing (usually plastic). Because of the relative proximity of these pads to each other on the same device it is easy for cross contamination to occur, causing unreliable results. This is called "runover" (i.e. when a reagent from one pad runs over another adjacent test pad). The present arts eliminates runover. The applicants novel approach to the solution of runover has not been taught prior to the present art and is the result of extensive research and development.

Result interpretation can be explained as follows. If the sample is positive, with a concentration of 1.0 mg/dL bromine or more, the following occurs. A drop of urine (approximately 50 uL) is applied at the starting point or origin of the strip. The urine then migrates to the opposite or terminal end of the strip. As the urine migrates across the lateral flow material (nitrocellulose) and comes into contact with the test pad (filter paper), the urine will saturate the pad and cause a chemical reaction between the impregnated chemicals and bromine(s) in the urine. A blue to purple color will develop on the test pad indicating a positive (greater than 1.0 mg/dL bromine) for the presence of bromine. This color can then be compared to a color chart showing the different colors from colorless (white background)) to a dark blue to purple depending upon the concentration of the bromine(s), if greater than 1.0 mg/dL. The reaction on the test pad is immediate thus the test results can be observed immediately.

If the sample is negative, with a concentration of less than 1.0 mg/dL of bromine present the following occurs. A drop of urine (approximately 50 uL) is applied at the starting point or origin of the strip. The urine then migrates to the opposite or terminal end of the strip. As the urine migrates across the lateral flow material and comes into contact with the test pad, the urine will saturate the pad and cause a chemical reaction between the impregnated chemicals and bromine. However, this example is for a negative result, thus, no reaction occurs and no color develops, indicating a negative result. This negative result color can then be compared to a color chart showing the different colors from no color developed (negative) to dark blue to purple depending upon the concentration of the bromine(s), if greater than 1.0 mg/dL. The reaction on the test pad is immediate thus the test results can be observed immediately.

Changes to the above reagent solution of example 3 can be made and still remain within the scope and function of this invention and will have similar results to examples I and 2 above. The indicator(s) and buffer(s) of example 3 can be replaced by all the examples and possible substitutions as illustrated in example 1.

This brief description of the present art illustrates a completely enabled device that would allow a physician, patient, and/or technician to quickly and easily determine the presence of the bromine in urine, providing a much needed advancement in the art of adulteration testing.

To briefly explain the present device as taught. The present art includes a device for the detection of bromine adulteration in a sample of urine submitted for drugs of abuse immunoassay testing the steps comprise of preparing a dry chemistry test means by successively impregnating a solid, carrier matrix with reagent solutions containing an indicator and a buffer, and drying the impregnated, solid carrier matrix. Finally, by dipping said dry chemistry test means into urine, one can observe the detectable response in the form of a color developed in the presence or absence of bromine. This present art also illustrates a unique device that will prevent cross contamination (runover) of test pads on the same dipstick, as well as a unique dry chemistry test pad lateral flow device hybrid. These methods can incorporate detectable responses in the visible color range to the human eye or in the visible light spectrum. In addition the present art can be used for clinical diagnostics of bromine toxicity. These methods have a wide sample choice other than urine, and can be replaced by any biological sample including serum, whole blood, cerebral spinal fluid, gastric fluid, hair homogenates, sweat extracts, saliva or other biological fluid.

EXAMPLE 4

This is a method for manufacturing a dry chemistry dipstick (test strip) with a solid carrier for the adulteration detection of oxidants in urine samples submitted for drugs of abuse analysis.

Filter paper is successively impregnated with the following solutions and dried at 25 degree C.:

Solution I bis[2-Hydroxyethyl]iminotris[hydroxymethyl]methane 20.9 g distilled water added to 100 mL total volume of solution pH the solution to a value between 1.0 and 12.5 preferably 5.0 lab notes: Buffer strength is preferably 0.01 Molar or greater

Solution 2
   m-Phenylenediamine (MPD) 0.01 g/L
   distilled water added to make 1000 mL total volume of solution
   lab notes: MPD needs to be in solution at a concentration 0.001 g/L or greater In this example a dipstick was prepared in accordance with the instant invention. The device comprised a paper carrier or solid matrix incorporated with the composition of solutions 1 and 2 above. Note that the concentrations of any of the following examples can be varied to suit the dipstick device format (dependent upon paper type, or use of semi-permeable membrane or other suitable material). This example is carried out using the following procedure. To produce the test means, a piece of Whatman 3 MM filter paper having approximate dimensions of 1 inch by 3 inches was impregnated with solution 1 by immersing the paper into solution 1. The paper was then dried by using forced air not exceeding 25° C. A second piece of Whatman 1 MM filter paper having approximate dimensions of 1 inch by 3 inches was impregnated with solution 2 by immersing the paper into solution 2. The paper was then dried by using forced air not exceeding 25° C. The dried papers are then laminated to each other by the use of a non-reactive (neutral adhesive). The dried, laminated papers are then applied to one side of a piece of double-sided adhesive transfer tape commercially available from 3M Company, St. Paul, Minn. 55144. The laminate is then slit into portions measuring 3 inches by 0.2 inches. One portion is then attached, via the unused adhesive side to a polystyrene sheet measuring about 1.5 inches by 3 inches and the resulting laminate is slit parallel to its short dimension to form test devices comprising a 1.5 inch oblong polystyrene strip carrying a square of the impregnated papers at one end, the other end serving as the handle. When the dipstick thus obtained is dipped into a urine submitted for drugs of abuse testing, and no uniform bluish color develops then no bromine(s) is present. Conversely, if any concentration of bromine(s) is present in the urine at a 0.1% v/v or greater a bluish color will develop thus confirming the presence of bromine(s).

In summary, Example 4 is as follows: the foregoing dry chemistry test strip (dipstick) method for the adulteration detection of bromine containing adulterants in a sample of urine submitted for drugs of abuse immunoassay testing comprises the steps of preparing a test means by successively impregnating a solid, carrier matrix with reagent solutions, drying the impregnated, solid test means, then dipping said dried test means into urine, and finally observing any color change in the presence or absence of bromine (s).

Changes to the above reagent solution of example 4 can be made and still remain within the scope and function of this invention and will have similar results to examples 1, 2 and 3 above. The indicator(s) and buffer(s) of example 4 can be replaced by all the examples and possible substitutions as illustrated in example 1.

This brief description of the present art illustrates a completely enabled device that would allow a physician, patient, and/or technician to quickly and easily determine the presence of an adulterant that contains bromine(s) in urine, providing a much needed advancement in the art of adulteration testing. The same devices as illustrated could be used for clinical diagnostic, industrial or other purposes using the same means.

To briefly explain the present device as taught. The present art includes a device for the detection of bromine or analogs of bromine (or other states of bromine such as sodium bromate, potassium bromate, etc.) in a sample of urine comprising the steps of preparing a dry chemistry test means by successively impregnating a solid, carrier matrix with reagent solutions containing an indicator and a buffer, and drying the impregnated, solid carrier matrix. Finally, by dipping said dry chemistry test means into urine, one can observe the detectable response in the form of a color developed in the presence or absence of bromine. This present art also illustrates a unique device that will prevent cross contamination (runover) of test pads on the same dipstick, as well as a unique dry chemistry test pad lateral flow device hybrid. These methods can incorporate detectable responses in the visible color range to the human eye or in the visible light spectrum. These methods have a wide sample choice other than urine, and can be replaced by any biological sample including serum, whole blood, cerebral spinal fluid, gastric fluid, hair homogenates, sweat extracts, saliva or other biological fluid.

It is understood that remarkable discovery of the new art formula and indicator(s) for bromine in the form of bromine in urine (as well as the other matrices mentioned) that was unknown prior to this art. The newly discovered and suitable indicators for the present art formula are one or more of the following; 1,2,3,4-tetrahydrobenzo(h)quinolin-3-ol, 1,2,3,4-tetrahydrobenzo(h)quinolone, 1,2,3,4-tetrahydrobenzo(h)quinaldine, 3-hydroxy-1,2,3,4-tetrahydrobenzo(h )quinolone, 3-hydroxy-N-methyl-1,2,3,4-tetrahydrobenzo(h)quinolone, 3-acetoxy-N-methyl-1,2,3,4-tetrahydrobenzo(h)quinolone, N-methyl-1,2,3,4-tetrahydrobenzo(h)quinolone, 1,3-phenylenediamine, 1,2,3,4-tetrahydroquinoline, 1,2,3,4-tetrahydroisoquinoline hydrochloride, 7,8-benzoquinoline, 1,2,3,4-tetrahydro-3-isoquinolinecarboxylicacid hydrochloride, 1,2,3,4-tetrahydro-1-napthylamine hydrochloride, napthylamine, N,N-dialkyl-alpha-napthylamine, phenolphthalin, 2,2'-Azino-di-(3-ethylbenzthiazolinesulfonic acid), 2,2'-Azino-di-(3-ethylbenzthiazolinesulfonic acid) diammonium salt, cyanoditoly tetrazolium chloride, 3,3'-diaminobenzidine, o-dianisidine, dimethoxybenzidine, 0-phenylenediamine, 3-amino-9-ethylcarbazole, 3,3'-5,5'-tetramethylbenzidine, dimethoxybenzidine, 8-hydroxyquinoline, m-phenylenediamine, 3-dimethylaminobenzoic acid, 5-aminosalicylic acid, and 4-chloro-1-napthol, and another indicator that is suitable for the present device is 4-aminoantipyrine in combination with one of the following compounds; p-hydroxybenzene sulfonate, p-hydroxybenzoic acid, n-ethyl-n-(2-hydroxy-3-sulfopropyl)-m-toluidine, n-ethyl-n-sulfopropyl-m-toluidine, 2-hydroxy-3,5-dichlorobenzenesulfonic acid, 3-hydroxy-2,4,6-triiodobenzoic acid, and 3-hydroxy-2,4,6-tribromobenzoic acid. In addition, some of the above indicators require a diazotizable amine in the form of sulfanilic acid, arsanilic acid, sulfanilamide, aminobenzoic acid, or other suitable amine. It is understood that the present arts discovery of the use of indicators such as the ones mentioned above or others that have not been mentioned that are sensitive to bromine oxidation-reduction reactions in biological matrices such as urine and are capable of producing a detectable response in the presence of a bromine oxidation-reduction reaction are within the present art. Therefore the use of a bromine oxidation-reduction indicator that is not mentioned here would fall within the spirit and scope of the present invention.

The subject invention, utilizing this concept, provides an extraordinary means for determining adulteration in a urine or other biological specimen submitted for drugs of abuse immunoassay with a single assay for bromine(s).

Furthermore, the subject invention will discourage additional attempts to use bromine(s) (or any form of bromine) as adulterants in samples to be tested via immunoassay systems.

In addition, and most importantly the present art provides a single test means that allows for the detection of all bromine forms that may be used as adulterants such as potassium bromate and sodium bromate to name a few with a single assay. This unique and marked advance in the art of adulteration will have an immediate beneficial impact on the drug and adulteration testing industry.

It is understood that variations or modifications in the following embodiments may be made by someone skilled in the art without departing from the spirit and scope of the invention. All such modifications and variations are to be included within the scope of the invention as defined in the appended claims:

I claim:

1. The method for the detection of bromine in a biological sample, wherein the biological sample is selected from the group consisting essentially of urine, serum, whole blood, cerebral spinal fluid, gastric fluid, hair homogenates, sweat extracts or saliva, consisting essentially of;

(A) preparing a dry chemistry test means by successively impregnating a solid, carrier matrix with reagent solutions consisting essentially of an indicator and a buffer, wherein the indicator is selected from the group consisting of 1,2,3,4-tetrahydrobenzo(h)quinolin-3-ol, 1,2,3,4-tetrahydrobenzo(h)quinolone, 1,3-phenylenediamine, 1,2,3,4-tetrahydroquinoline, 1,2,3,4-tetrahydroisquinoline hydrochloride, 7,8-benzoquinoline, [1,2,3,4-tetrahydro-3-isoquinolinecarboxylicacid hydrochloride,] 1,2,3,4-tetrahydro-1-napthylamine hydrochloride, napthylamine, 2,2'-Azino-di-(3-ethylbenzthiazolinesulfonic acid), 2,2'-Azino-di-(3-ethylbenzthiazolinesulfonic acid) diammonium salt, 3,3'-diaminobenzidine, o-dianisidine, dimethoxybenzidine, 0-phenylenediamine, 3-amino-9-ethylcarbazole, 3,3'-5,5'-tetramethylbenzidine, dimethoxybenzidine, 8-hydroxyquinoline, m-phenylenediamine, 3-dimethylaminobenzoic acid, 5-aminosalicylic acid, 4-chloro-1-napthol, diazotizable amine, sulfanilic acid, arsanilic acid, sulfanilamide, aminobenzoic acid or 4-aminoantipyrine in combination with one of the following compounds; p-hydroxybenzene sulfonate, p-hydroxybenzoic acid, n-ethyl-n-(2-hydroxy-3-sulfopropyl)-m-toluidine, n-ethyl-n-sulfopropyl-m-toluidine, 2-hydroxy-3,5-dichlorobenzenesulfonic acid, 3-hydroxy-2,4,6-triiodobenzoic acid, and 3-hydroxy-2,4,6-tribromobenzoic acid (B) drying the impregnated solid carrier matrix;

(C) dipping said chemistry test means into the biological sample; and (D) observing a detectable response in the form of a color developed in the presence or absence of bromine, wherein the color is observable to the human eye or visible light spectrum.

2. The method for the detection of bromine in a biological sample, wherein the biological sample is selected from the group consisting essentially of urine, serum, whole blood, cerebral spinal fluid, gastric fluid, hair homogenates, sweat extracts or saliva, consisting essentially of;

(A) preparing a dry chemistry test means by successively impregnating a solid, carrier matrix with reagent solutions consisting essentially of an indicator and a buffer, wherein the buffer is selected from the group consisting of citrate, borate, borax, sodium tetraborate decahydrate, sodium perchlorate, sodium chlorate, sodium carbonate, (Tris[hydroxymethyl] aminomethane), (2-[N-Morpholino]ethanesulfonic acid), (bis[2-Hydroxyethyl]iminotris[hydroxymethyl] methane; 2-bis[2-hydroxyethyl]amino-2-[hydroxymethyl-1,3-propanediol), (N-[2-Acetamidol]-2-iminodiacetic acid; N-[Carbaoylmethyl]iminodiacetc acid), (2-[(2-Amino-2-oxoethyl)amino]ethanesulfonic acid; N-[2-Acetamido]-2-aminoethanesulfonic acid), (PiperazineN-N'-bis[2-ethanesulfonic acid)]; 1,4-Piperzinedethanesulfoic acid), (3-[N-Morpholinol]-2-hydroxypropanesulfonic acid), (1,3-bis[tris (Hydroxymethyl)methylamino]propane), (N,N-bis[2-Hydroxyethyl]-2-aminoethaesulfonic acid; 2-bis(2-Hydroxyethyl)amino]ethanesulfonic acid), (3-[N-Morpholino]propanesulfonic acid), (N-tris [Hydroxymethyl]methyl-2-aminomethanesulfonic acid; 2[2-Hysroxy-1,1-bis(hydroxymethyl)-ethyl] amino)ethanesulfonic acid), (3-[N,N-bis(2-Hydroxyethyl)amino]-2-hydroxypropanesulfonic acid), (3-[N-tris(Hydroxyethyl)methylamino]-2-(hydroxypropanesulfonic acid), (N-[2-Hydroxythyl] piperazine-N'-[2Hydroxypropanesulfonic acid]), (Piperazine-N,N'-bis[2-hydroxypropanesulfonic acid]), (N-[2-Hydroxyethyl]piperazine-N'-[3-propanesulfonic acid), (triethanolamine), (N-tris[Hydroxymethyl] methyllycine; N-[2-Hydroxy-1-1-bis(hydroxymethyl) etyyl]glycine), (N,N-bis[2-Hydroxyethyl]glycine), (N-tris[Hydroxymethyl]methyl-3-aminopropanesulfonic acid; ([2-Hydroxy-1,1-bis (hydroxymethyl)ethyl]amino)-1-propanesulfonic acid), (3-[(1,1-Dimethyl-2-hydroxyethyl)amino]-2-hydroxypropanesulfonic acid), (2-[N-Cyclohexylamino]ethanesulifonic acid), (3-[Cyclohexylamino]-2-hydroxy-1-propanesulfonic acid), 2-Amino-2-ethyl-1-propanol, (3-[cyclohexylamino]-1-propanesulfonic acid), hydrochloric acid, phosphoric acid, lactic acid, sulfuric acid, nitric acid, chromic acid, boric acid, citric acid, oxalic acid, tartaric acid, succinic acid, perchloric acid, potassium hydrogen tartrate, potassium hydrogen phthalate, calcium hydroxide, phosphate, bicarbonate, sodium hydroxide, potassium hydroxide, tartrate, oxalate or succinate (B) drying the impregnated solid carrier matrix;

(C) dipping said chemistry test means into the biological sample; and (D) observing a detectable response in the form of a color developed in the presence or absence of bromine, wherein the color is observable to the human eye or visible light spectrum.

* * * * *